(12) United States Patent
Ito

(10) Patent No.: US 10,994,094 B2
(45) Date of Patent: May 4, 2021

(54) CATHETER

(71) Applicant: TERUMO KABUSHIKI KAISHA, Tokyo (JP)

(72) Inventor: Takashi Ito, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 148 days.

(21) Appl. No.: 16/052,978

(22) Filed: Aug. 2, 2018

(65) Prior Publication Data

US 2018/0344975 A1 Dec. 6, 2018

Related U.S. Application Data

(63) Continuation of application No. PCT/JP2017/002641, filed on Jan. 26, 2017.

(30) Foreign Application Priority Data

Feb. 5, 2016 (JP) .............................. JP2016-021365

(51) Int. Cl.
*A61M 25/00* (2006.01)
*A61M 25/01* (2006.01)

(52) U.S. Cl.
CPC ........ *A61M 25/0053* (2013.01); *A61M 25/00* (2013.01); *A61M 25/0012* (2013.01); *A61M 25/0105* (2013.01); *A61M 25/0045* (2013.01)

(58) Field of Classification Search
CPC .......... A61M 25/0012; A61M 25/0045; A61M 25/005; A61M 25/0053; A61M 25/0015
See application file for complete search history.

(56) References Cited

U.S. PATENT DOCUMENTS

| | | |
|---|---|---|
| 2002/0026128 A1 | 2/2002 | White et al. |
| 2003/0139689 A1 | 7/2003 | Shturman et al. |
| 2007/0083132 A1 | 4/2007 | Sharrow |

FOREIGN PATENT DOCUMENTS

| | | |
|---|---|---|
| EP | 0397459 A1 | 11/1990 |
| EP | 1933921 A1 | 6/2008 |
| JP | H07-323090 A | 12/1995 |
| JP | H08-071157 A | 3/1996 |

(Continued)

OTHER PUBLICATIONS

International Search Report (PCT/ISA/210) dated Apr. 11, 2017, by the Japanese Patent Office as the International Searching Authority for International Application No. PCT/JP2017/002641.

(Continued)

*Primary Examiner* — Deanna K Hall
(74) *Attorney, Agent, or Firm* — Buchanan Ingersoll & Rooney PC

(57) ABSTRACT

A catheter is disclosed, which includes an inner tube, and a coil tube disposed on an outer peripheral side of the inner tube, the inner tube being a coil obtained by winding a wire. In addition, in the coil tube, a first coil and a second coil are arranged concentrically with each other. The first coil and the second coil have mutually different winding directions of the wire. Then, the inner tube and the coil tube are rotatable relative to each other around a central axis of the coil tube. In addition, in a natural state where no external force is applied to the catheter, a gap is formed between the inner tube and the coil tube.

20 Claims, 10 Drawing Sheets

(56) References Cited

FOREIGN PATENT DOCUMENTS

| | | | |
|---|---|---|---|
| JP | 2002-272852 | * | 9/2002 |
| JP | 2002-272852 A | | 9/2002 |
| JP | 200558304 A | | 3/2005 |
| JP | 2011-177231 | * | 9/2011 |
| JP | 2011177231 A | | 9/2011 |
| WO | 2007/044783 A1 | | 4/2007 |

OTHER PUBLICATIONS

Extended Search Report issued by the European Patent Office in corresponding European Patent Application No. 17747290.9-1132 dated Mar. 26, 2020 (8 pages).
Notification of Reasons for Refusal issued by the Japanese Patent Office in corresponding Japanese Patent Application No. 2017-565505 dated May 26, 2020 (6 pages including partial English translation).
Office Action (Notice of Reasons for Refusal) dated Dec. 22, 2020, by the Japanese Patent Office in corresponding Japanese Patent Application No. 2017-565505 and an English Translation of the Office Action. (7 pages).

* cited by examiner

CATHETER

CROSS-REFERENCES TO RELATED APPLICATIONS

This application is a continuation of International Application No. PCT/JP/2017/002641 filed on Jan. 26, 2017, which claims priority to Japanese Application No. 2016-021365 filed on Feb. 5, 2016, the entire contents of both of which is incorporated herein by reference.

TECHNICAL FIELD

The present disclosure generally relates to a catheter inserted into a biological lumen, and particularly relates to a catheter for guiding a medical device such as a treatment catheter to a target site in a lumen of a body/living body.

BACKGROUND DISCUSSION

In the medical field, various forms of treatment are performed using an elongated hollow tubular medical device called a catheter (refer to JP-A-2011-177231).

As this treatment method, a length properly of the catheter is utilized. The treatment method includes a method of directly administering a medicine to a target lesion (lesion area) by a micro catheter, a support catheter, an angiographic catheter or a guiding catheter, a method of stuffing and closing an aneurysm, a bleeding place, or nutrition blood vessel, and a method in which a treatment catheter whose distal end has an attached balloon capable of being dilated upon pressurization is caused to reach a stenosed site inside a blood vessel through the guiding catheter, and then, the stenosed site is widened and opened by dilating the balloon upon pressurization.

The catheter disclosed in JP-A-2011-177231 includes a catheter body having a soft tube and a coil incorporated into the tube and functioning as a core, and a hub disposed in a proximal portion of the catheter body. When the catheter is pushed forward (or advanced) into the blood vessel, for example, the hub is rotated in order to change a direction of a distal end of the catheter body, and a rotational force is transmitted to the catheter body so as to perform an operation for rotating the distal end. When this rotary operation is performed, the coil functions as the core. Accordingly, the rotational force may be transmitted to the distal end (torque transmission).

However, the tube of the catheter body can be made of a material, which is flexible and relatively soft. Accordingly, depending on a length of the tube of the catheter body, the rotational force for rotating the hub may not be sufficiently transmitted to the distal end of the catheter body. As a result, operability becomes relatively poor.

SUMMARY

A catheter is disclosed which has relatively excellent operability.

The catheter disclosed here may involve the following aspects (1) to (9).

(1) A catheter includes an inner tube, and a coil tube disposed on an outer peripheral side of the inner tube and includes a coil obtained by winding a wire. The coil tube has at least one first coil, and at least one second coil which is located concentrically with the first coil and whose winding direction of the wire is different from that of the first coil. The inner tube and the coil tube are rotatable relative to each other around a central axis of the coil tube.

(2) In the catheter according to (1) described above, in a natural state where no external force is applied to the catheter, a gap is formed between the inner tube and the coil tube.

(3) In the catheter according to (1) or (2) described above, the at least one second coil is located inside the at least one first coil.

(4) The catheter according to any one of (1) to (3) described above further has a third coil disposed inside the at least one second coil and obtained by winding the wire in a direction different from that of the at least one second coil.

(5) In the catheter according to any one of (1) to (4) described above, the catheter is inserted into a living body from a distal side. The catheter further includes a rotary operation unit fixed to a proximal portion of the coil tube and performing a rotary operation so as to transmit a rotational force of the rotary operation unit to the coil tube.

(6) In the catheter according to (5) described above, the rotary operation unit has a tubular operation tube. A central axis of the operation tube coincides with the central axis of the coil tube.

(7) In the catheter according to (5) described above, the rotary operation unit has a first gear fixed to the coil tube, and a second gear meshing with the first gear. The second gear performs the rotary operation so as to rotate the coil tube.

(8) The catheter according to any one of (1) to (7) described above further has an outer tube disposed on an outer peripheral side of the coil tube. The outer tube and the coil tube are rotatable relative to each other around a central axis of the coil tube.

(9) In the catheter according to (8) described above, an outer peripheral portion of the outer tube is subjected to hydrophilic treatment for improving a hydrophilic property.

According to the present disclosure, the coil tube is rotatable relative to the inner tube. Therefore, the coil tube performs a rotary operation so as to help enable the overall catheter to perform the rotary operation. That is, the coil tube is responsible for transmitting a rotational force.

In addition, the coil tube can include the first coil and the second coil which have mutually different winding directions. Accordingly, if the coil tube is rotated in a direction the same as the winding direction of the first coil, a force is applied to the first coil so that the diameter of the first coil expands and the length of the first coil is shortened in a length (i.e., axial direction). In contrast, a force is applied to the second coil, and the second coil is tightened so that the diameter of the second coil contracts and the length of the second coil is elongated in a length (i.e., axial direction). On the other hand, if the coil tube is rotated in a direction opposite to the winding direction of the first coil, the force is applied to the first coil so that the diameter of the first coil contracts and the length of the first coil is elongated in a length (i.e., axial direction). In contrast, the force is applied to the second coil so that the diameter of the second coil expands and the length of the second coil is shortened in a length (i.e., axial direction).

In this way, according to the present disclosure, even if the coil tube is rotated in any direction, the coil tube has a portion to which the rotational force may be transmitted. Therefore, the rotational force can be efficiently transmitted to a distal end of the coil tube.

In addition, in a case where the third coil having the winding direction different from that of the second coil is present, the force is applied to the third coil so that the diameter of the third coils expands and the length of the third coil is shortened in a length direction (i.e., axial direction).

In addition, in a case where the respective wires of the coils are wound in close contact with each other as much as possible, the coil freely extends in the length direction, but the coil has no play in a compression direction. Therefore, rotary stress on an operator's hand side has no escape, and the rotary stress can be transmitted to the distal end.

Furthermore, since the inner tube is present, passing ability of a guide wire or a treatment device within inner tube the can be improved, thereby facilitating injection of a liquid such as a contrast agent through the hollow portion of the inner tube.

A catheter is disclosed, the catheter comprising: an inner tube; a coil tube disposed on an outer peripheral side of the inner tube, the coil tube having a first coil, a second coil, and a third coil, the second coil being located concentrically with the first coil and whose winding direction is different from that of the first coil, and the third coil being disposed inside the second coil, and wherein the third coil is wound in a direction different from that of the second coil, the inner tube and the coil tube being rotatable relative to each other around a central axis of the coil tube; and an outer tube disposed on an outer peripheral side of the coil tube, the outer tube and the coil tube being rotatable relative to each other around the central axis of the coil tube.

A method is disclosed for guiding a catheter to a target site in a living body, the method comprising: inserting the catheter into a living body, the catheter including an inner tube and a coil tube disposed on an outer peripheral side of the inner tube, the coil tube being a wound wire coil, the coil tube having at least one first coil and at least one second coil, the at least one second coil being located concentrically with the at least first coil, and a winding direction of the at least one second coil being a different direction from a winding direction of the at least one first coil; and rotating the coil tube relative to the inner tube around a central axis of the coil tube while advancing the catheter in a biological lumen of the living body.

According to the above-described configuration, the catheter of the present disclosure can be excellent in operability such as torque transmission performance and directional selectivity.

BRIEF DESCRIPTION OF THE DRAWINGS

FIGS. 5A and 5B are partial cutaway views of the side view of the coil tube illustrated in FIG. 1, wherein FIG. 5A illustrates a state where the coil tube is rotated in a direction of an arrow B, and FIG. 5B illustrates a state where the coil tube is rotated in a direction of an arrow C.

DETAILED DESCRIPTION

Set forth below reference to the drawings is a detailed description of embodiments of a catheter and a method for making the catheter representing an example of the inventive catheter and method disclosed here.

First Embodiment

Hereinafter, for convenience of description, an upper side in FIGS. 1 to 5B (similarly applicable to FIGS. 6 to 14) is referred to as "up" or "upward", a lower side is referred to as "down" or "downward", a left side is referred to as "left", "distal side", or a "distal end", and a right side is referred to as "right", "proximal side", or a "proximal end". That is, in the catheter, the catheter body side is referred to as the "distal end" and a side opposite to the "distal end" (rotary operation unit side) is referred to as the "proximal end".

Figure 1:
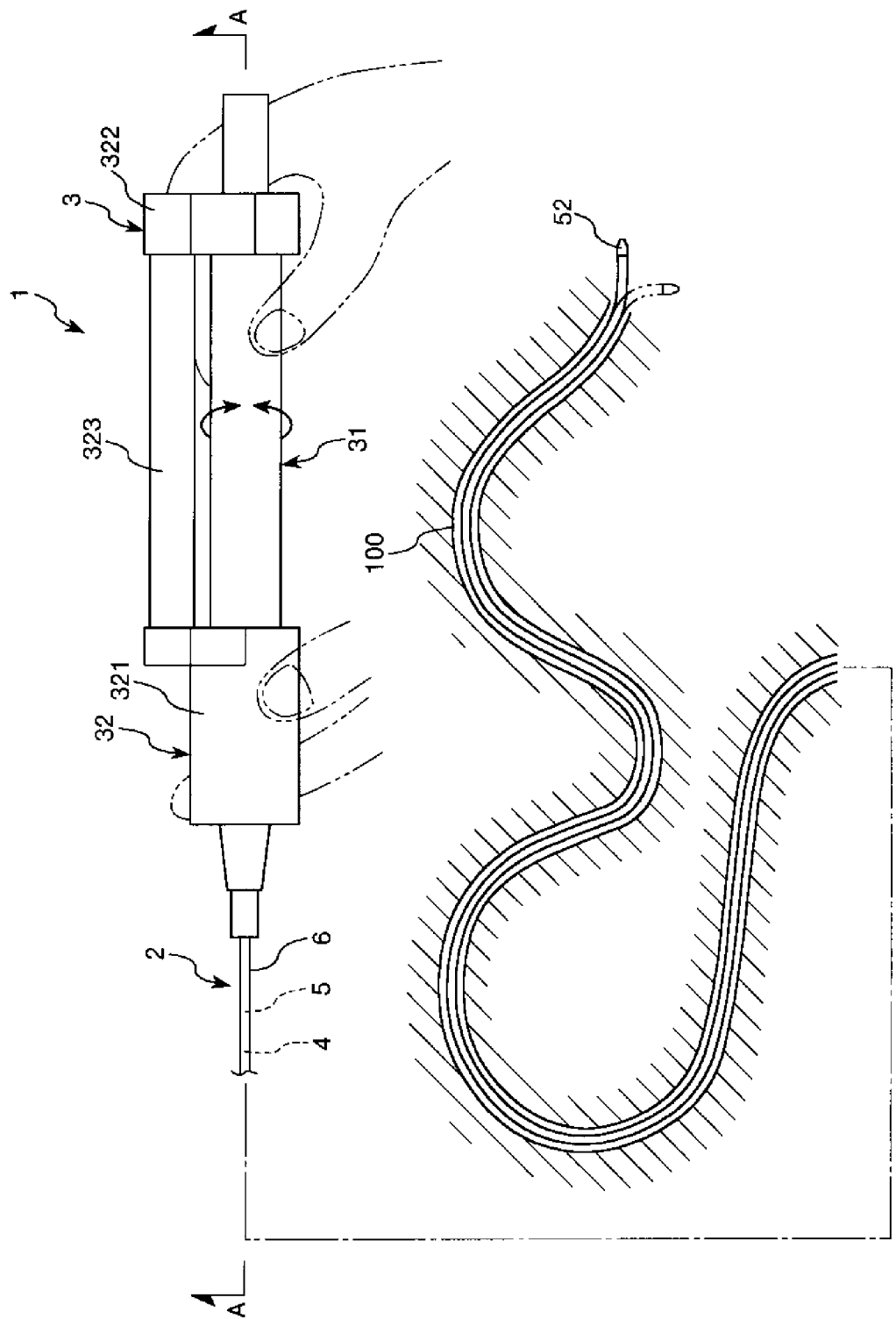
FIG. 1 is a side view illustrating a catheter (first embodiment) according to the present disclosure.

A catheter 1 illustrated in FIG. 1 includes a catheter body 2 inserted into a blood vessel (i.e., body lumen) 100, and a rotary operation unit 3 disposed in a proximal portion of the catheter body 2.

Figure 2:
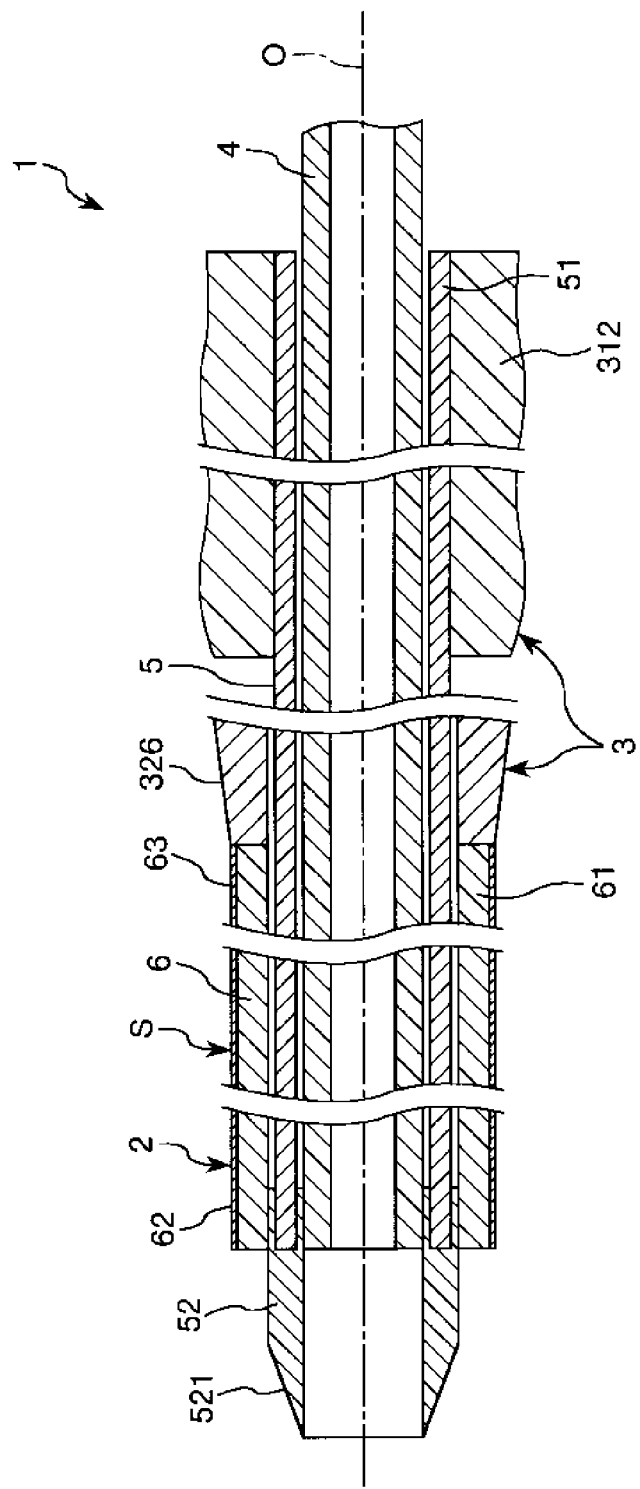
FIG. 2 is a longitudinal sectional view of a catheter body included in the catheter illustrated in FIG. 1.

As illustrated in FIG. 2, the catheter body 2 is flexible, and has a triple-tube structure having an inner tube 4, a coil tube 5, and an outer tube 6. In addition, the inner tube 4, the coil tube 5, and the outer tube 6 are concentrically arranged in this order (i.e., the inner tube 4, the coil tube 5, and the outer tube 6) from the inside around a central axis O of the catheter body 2.

Figure 3:
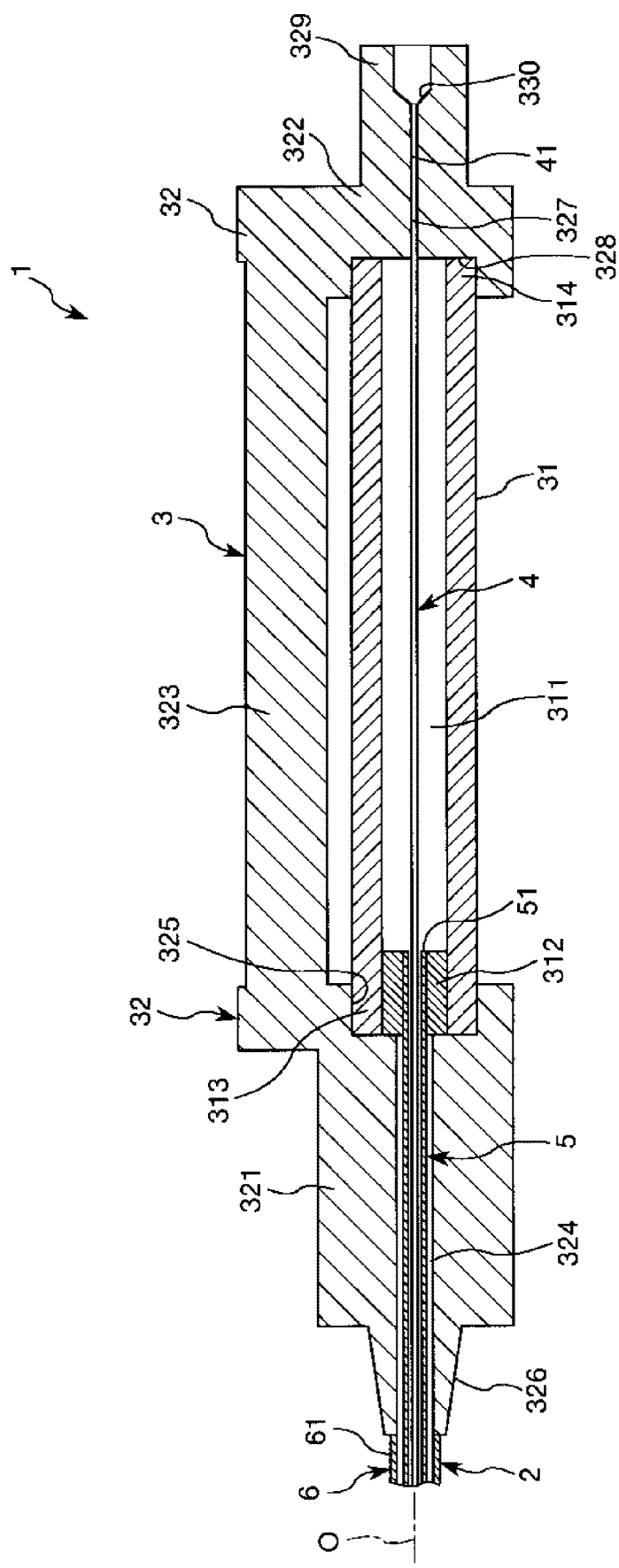
FIG. 3 is a sectional view taken along line A-A in FIG. 1.

As illustrated in FIGS. 2 and 3, the inner tube 4 can be a flexible tube. In addition, in the inner tube 4, a proximal portion 41 of the inner tube 4 is fixed to the rotary operation unit 3.

The coil tube 5 can be a coil. The coil tube 5 is shorter than the inner tube 4, and a proximal portion 51 of the coil tube 5 is located on a distal side from the proximal portion 41 of the inner tube 4. Therefore, the proximal portion 41 of the inner tube 4 is exposed from a proximal opening of the coil tube 5.

In addition, a tubular distal tip 52 is fixed to the distal portion of the coil tube 5. The distal tip 52 has a tubular shape, and is located on the distal side from the inner tube 4 and the outer tube 6. In addition, the distal tip 52 has a tapered portion 521 whose outer diameter gradually decreases toward the distal side. In this manner, for example, the distal tip 52 can enter a stenosed site relatively easily.

As illustrated in FIGS. 2 and 3, the outer tube 6, for example, can be a flexible tube. The outer tube 6 is shorter than the coil tube 5, and a proximal portion 61 of the outer tube 6 is located on the distal side from the proximal portion 51 of the coil tube 5. Therefore, the proximal portion 51 of the coil tube 5 is exposed from a proximal opening of the outer tube 6. In addition, in a natural state where no external force is applied to the catheter 1, a gap is formed between the inner tube 4 and the coil tube 5. In this manner, the inner tube 4 can be prevented from hindering the rotation of the coil tube 5.

In addition, as illustrated in FIG. 2, the outer tube 6 has a distal side tubular portion 62 disposed in the outer peripheral portion and located on the distal side from a central portion S of the outer tube 6, and a proximal side tubular portion 63 located on the proximal side from the central portion S.

The distal side tubular portion 62 functions as a base layer of a hydrophilic coat. For example, the distal side tubular portion 62 can be made of a material having relatively high affinity for the hydrophilic coat, such as polyurethane. In this manner, the affinity between the outer tube 6 and the hydrophilic coat can be improved. Accordingly, the hydrophilic coat can be prevented from being separated from the outer tube 6.

The proximal side tubular portion 63, for example, can be made of a relatively high rigid resin material such as nylon and polyurethane. In this manner, the outer tube 6 can be protected.

As a material of the inner tube 4, the outer tube 6, and the distal tip 52, a flexible resin material can be used. However, it can be particularly preferable to mainly use at least one type selected from the group including a fluorine-based resin such as high-density polyethylene, polyolefin such as polypropylene, polyamide such as nylon 66, polyurethane, polyesters such as polyethylene terephthalate, polybutylene terephthalate, and polycyclohexane terephthalate, polytetrafluoroethylene, and an ethylene-tetrafluoroethylene copolymer. The inner tube 4, the outer tube 6, and the distal tip 52 may be a multi-layer tube having a coil which includes the above-described resin material or a metal material or a braided material.

The materials of the inner tube 4, the outer tube 6, and the distal tip 52 are materials having relatively low frictional resistance (low-friction material). Accordingly, the inner tube 4 can be made of a material having relatively low frictional resistance. Therefore, for example, it is possible to easily and reliably perform an operation for inserting the guide wire into a hollow portion (i.e., lumen) of the inner tube 4 or an operation for pulling out the guide wire from the inner tube 4.

The material of the inner tube 4, the outer tube 6, and the distal tip 52 may contain a particle, for example, a radiopaque material (radiopaque substance). In this manner, visibility of the catheter body 2 is improved under X-ray fluoroscopy. For example, the radiopaque material can include tungsten, bismuth oxide, and barium sulfate.

In addition, a coating film formed of a silicone resin may be formed on an inner surface of the inner tube 4. In this manner, a frictional force is further reduced on the inner surface of the inner tube 4.

In addition, in order to reduce friction between the coil tube 5 and the inner tube 4, the inner peripheral surface of the coil tube 5 or the outer peripheral surface of the inner tube 4 may be coated with a silicone resin, a hydrophilic coat, or lubricating oil.

In addition, the hydrophilic coat is not particularly limited. It is possible to use a hydrophilic polymer material which shows lubrication when the material comes into contact with a liquid such as blood and saline. In this manner, the frictional resistance of the catheter body 2 can be reduced, and sliding ability is further improved. Accordingly, an operation for inserting the catheter body 2 into the meandering blood vessel 100 can be performed relatively easily.

The above-described hydrophilic polymer material is not particularly limited. However, for example, cellulose-based polymeric substances (for example, hydroxypropyl cellulose), polyethyleneoxide-based polymeric substances (for example, polyethylene glycol), maleic anhydride-based polymeric substances (for example, methylvinylether-maleic anhydride copolymer), acrylamide polymeric substances (for example, dimethylacrylamide-glycidyl methacrylate copolymer), and water-soluble nylon can be used alone or in combination of two or more materials.

In addition, the above-described hydrophilic coat may be omitted, and the outer peripheral portion of the outer tube 6 may be subjected to hydrophilic treatment for improving a hydrophilic property. For example, the hydrophilic treatment includes physical activation treatment such as plasma treatment, glow discharge, corona discharge, and ultraviolet irradiation.

In addition, as a configuration material of the coil tube 5, a resin material may be used, or a metal material may be used. However, from a viewpoint of improving rigidity, it can be preferable to use the metal material.

For example, the above-described metal material includes stainless steel (for example, SUS304, SUS303, SUS316, SUS316L, SUS316J1, SUS316J1L, SUS405, SUS430, SUS434, SUS444, SUS429, SUS430F, and SUS302), a piano wire, a cobalt alloy, and a Ni—Ti alloy.

In the catheter body 2 configured in this way, the coil tube 5 is disposed so as not to be fixed to the inner tube 4 and the outer tube 6 throughout an extension line in a longitudinal direction of the catheter body 2. In this manner, the coil tube 5 is rotatable relative to the inner tube 4 and the outer tube 6.

Next, the rotary operation unit 3 will be described.

As illustrated in FIG. 3, the rotary operation unit 3 has an operation tube 31 and a support portion 32 which rotatably supports the operation tube 31.

The operation tube 31 can be a cylindrical member. The operation tube 31 is located on an extension line of the proximal side of the central axis O of the catheter body 2. In addition, a portion of the inner tube 4, which is exposed from the proximal ends of the coil tube 5 and the outer tube 6, is inserted into a lumen portion 311 of the operation tube 31.

In addition, a bearing 312 is disposed inside and on the distal side of the lumen portion 311 of the operation tube 31. The proximal portion 51 of the coil tube 5 is fixed to the operation tube 31 via the bearing 312. In this manner, if the operation tube 31 is rotated, the coil tube 5 is rotated around the central axis O.

In addition, the central axis of the operation tube 31 coincides with the central axis O (central axis of the coil tube 5) of the catheter body 2. In this manner, a rotational force which rotates the operation tube 31 can be efficiently transmitted to the coil tube 5.

The support portion 32 has a distal side support portion 321 located on the distal side, a proximal side support portion 322 located on the proximal side, and an interlock portion 323.

The distal side support portion 321 has a substantially cylindrical shape, and a portion of the inner tube 4 and the coil tube 5, which is exposed from the proximal portion of the outer tube 6, is inserted into a lumen portion 324 of the distal side support portion 321. In addition, the distal side support portion 321 has a concave portion 325 open on the proximal side. A distal portion 313 of the operation tube 31 is rotatably inserted into the concave portion 325.

In addition, the distal portion of the distal side support portion 321 serves as a tapered portion 326 whose outer diameter gradually decreases toward the distal side. In this manner, for example, when used by inserting the tapered portion 326 into a guiding catheter, a contrast catheter, or a micro catheter, the tapered portion 326 can be fitted to a catheter hub of the guiding catheter, thereby enabling a medical procedure to be stably carried out. In addition, the proximal portion 61 of the outer tube 6 is fixed to the distal end of the tapered portion 326. The tapered portion 326 may be omitted, and the proximal portion 61 of the outer tube 6 may be directly fixed to the distal side support portion 321.

The proximal side support portion 322 is fixed to the distal side support portion 321 by the interlock portion 323. In addition, in the proximal side support portion 322, the inner tube 4 is inserted into and fixed to a lumen portion 327 of proximal side support portion 322. In addition, the proximal side support portion 322 has a concave portion 328 open on the distal side. A proximal portion 314 of the operation tube 31 is rotatably inserted into the concave portion 328.

In addition, the proximal side support portion 322 has a protruding portion (hub) 329 protruding in a cylindrical shape toward the proximal side. For example, other medical instruments such as a syringe can be connected to the protruding portion 329. A proximal portion of the lumen portion 327 has a tapered portion 330 whose inner diameter increases toward the proximal side. Accordingly, the other medical device can be fitted to tapered portion 330, and a connection state between the medical device and the tapered portion 330 can be maintained.

For example, as illustrated in FIG. 1, in a state where the distal side support portion 321 is gripped and fixed with a left hand, the rotary operation unit 3 can be used while the operation tube 31 is rotated with a right hand. In this manner, the coil tube 5 is rotated by performing a rotary operation. The operation tube 31 may be operated with the left hand, and the guide wire may be used while being operated with the right hand.

Next, the coil tube 5 will be described in detail.

Figure 4:
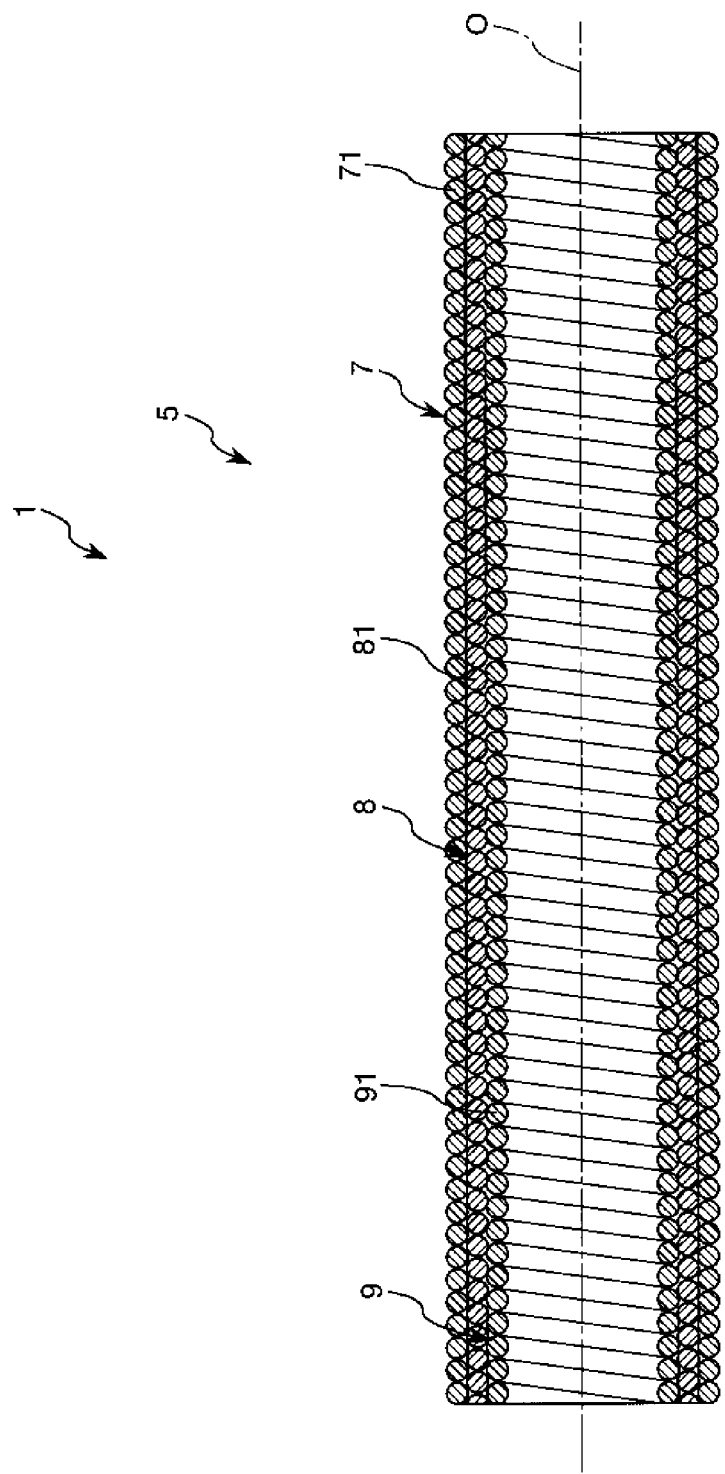
FIG. 4 is a longitudinal sectional view of a coil tube illustrated in FIG. 1.

As illustrated in FIG. 4, the coil tube 5 has a triple-tube structure having a first coil 7, a second coil 8, and a third coil 9 (third coil). The first coil 7, the second coil 8, and the third coil 9 are arranged in this order from the outside (i.e., outer diameter). In addition, in the first coil 7 and the second coil 8, and in the second coil 8 and the third coil 9, the respective outer peripheral portions and the respective inner peripheral portions are in contact with each other.

In addition, the first coil 7, the second coil 8, and the third coil 9 may be configured so that radially overlapping portions are fixed to each other. Alternatively, all of the first coil 7, the second coil 8, and the third coil 9 may be configured so that longitudinally intermediate portions are not fixed to each other and end portions are fixed to each other. In particular, if the end portions of the first coil 7, the second coil 8, and the third coil 9 are fixed to each other, the end portions of the coils 7, 8, 9 can be prevented from moving in mutually different directions. For example, a fixing method of the coils 7, 8, 9 can include quenching, fusion bonding, brazing, adhesion, and a method of collectively coating all of the coils 7, 8, 9 with a resin layer.

Here, a winding direction differs between the first coil 7 and the second coil 8. When the first coil 7 is viewed from the proximal side, one wire 71 is wound counterclockwise (direction of an arrow B in FIG. 5A) from the proximal side toward the distal side. When the coil 8 is viewed from the proximal side, one wire 81 is wound clockwise (direction of an arrow C in FIG. 5B) from the proximal side toward the distal side.

In addition, the winding direction differs between the second coil 8 and the third coil 9. When the third coil 9 is viewed from the proximal side, one wire 91 is wound counterclockwise (direction of the arrow B in FIG. 5A) from the proximal side toward the distal side. In accordance with an aspect, the first coil 7 and the third coil 9 have mutually the same winding direction.

Figure 5A:
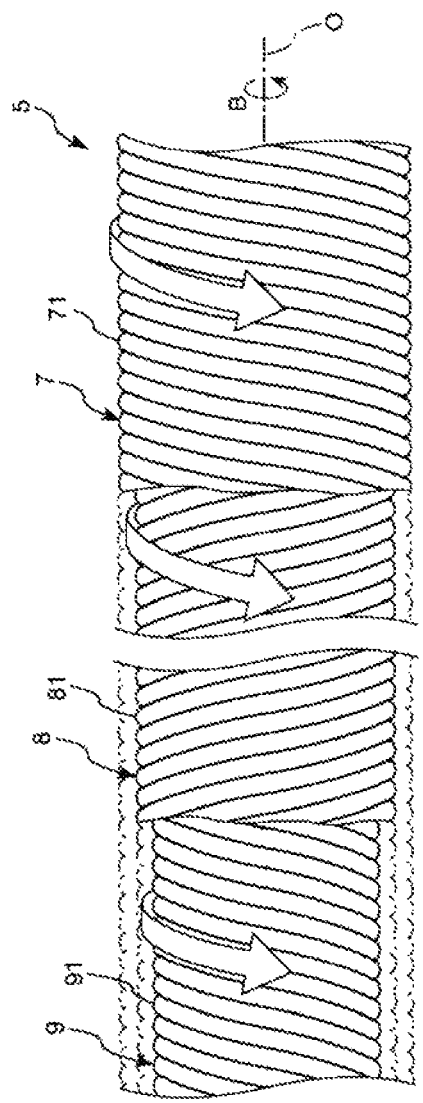

If the first coil 7 is rotated in the direction the same as the winding direction of the first coil 7, that is, in the direction of the arrow B in FIG. 5A, a force is applied to the first coil 7 so that the diameter of the first coil 7 expands and the length of the first coil 7 is shortened in the length direction. In contrast, a force is applied to the coil 8 whose winding direction is different from that of the first coil 7, and the second coil 8 is tightened so that the diameter of the second coil 8 contracts and the length of the second coil 8 is lengthened in the length direction. A force is applied to the third coil 9 whose winding direction is different from that of the second coil 8 so that the diameter of the third coils 9 expands similarly to the first coil 7 and the length of the third coil 9 is shortened in the length direction.

Figure 5B:
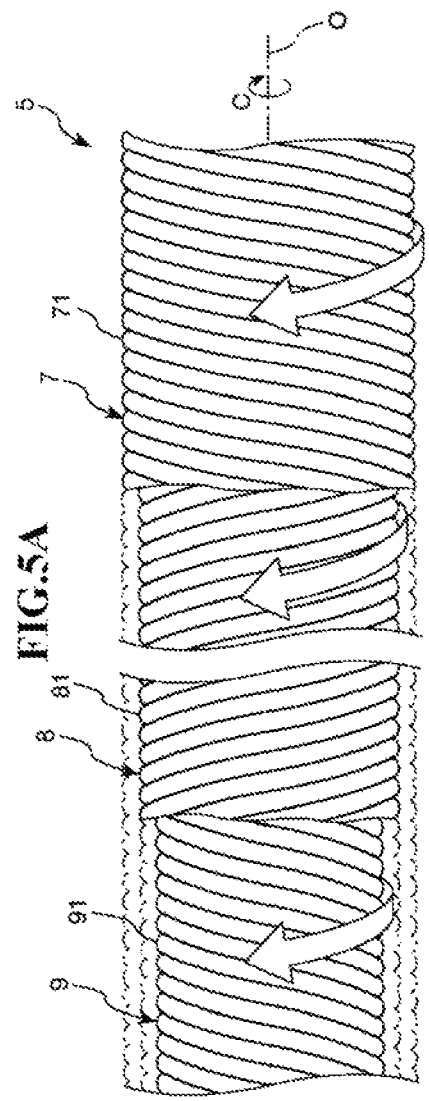

Conversely, if the first coil 7 is rotated in a direction opposite to the winding direction of the first coil 7, that is, in the direction of the arrow C in FIG. 5B, a force is applied to the first coil 7, and the first coil 7 is tightened so that the diameter of the first coil 7 contracts and the length of the first coil 7 is lengthened in the length direction. In contrast, a force is applied to the second coil 8 whose winding direction is different from that of the first coil 7 so that the diameter of the second coil 8 expands and the length of the second coil 8 is shortened in the length direction. A force is applied to the third coil 9 whose winding direction is different from that of the second coil 8, and the third coil 9 is tightened similarly to the first coil 7 so that the diameter of the third coil 9 contracts and the length of the third coil 9 is lengthened in the length direction.

In addition, the respective wires 71, 81, and 91 (i.e., first wire 71, second wire 81, and third wire 91) are wound so that the wires adjacent to each other in the length direction are in close contact with each other as much as possible. Accordingly, the coils 7, 8, 9 freely extend in the length direction, but the coils have no play in a compression direction. Therefore, rotary stress on an operator's hand side has no escape, and the rotary stress is transferred to the distal end.

According to this configuration, even if the rotary operation is performed in any direction of the direction of the arrow B and the direction of the arrow C in FIGS. 5A and 5B, the coil tube 5 has a portion which efficiently transmits the rotational force. Accordingly, for example, as illustrated in FIG. 1, when an orientation of the distal end of the catheter 1 is changed, even if the rotary operation is performed in any direction, the rotational force is reliably transmitted to the distal end of the coil tube 5, and the orientation of the distal portion of the catheter 1 can be changed together with the inner tube 4 and the outer tube 6. As a result, the catheter 1 is excellent in operability such as torque transmission performance and directional selectivity.

In addition, a fixing force of the first coil 7, the second coil 8, and the third coil 9 can be stronger than the force applied in the length direction. Therefore, the rotational force is effectively transmitted to the distal portion.

In addition, as described above, the coil tube 5 is disposed so as not to be fixed to the inner tube 4 and the outer tube 6 over the entire length of the coil tube 5. Therefore, the coil tube 5 can be independently rotated. Therefore, it is possible to prevent the above-described rotation of the coil tube 5 from being hindered by the inner tube 4 and the outer tube 6. Therefore, excellent operability can be realized, for example, such as excellent torque transmission performance and directional selectivity of the catheter 1.

In accordance with an aspect, the rigidity of the coil tube 5 can be higher than the rigidity of the inner tube 4 and the outer tube 6. In this manner, if the coil tube 5 is rotated, the coil tube 5 can be reliably rotated relative to the inner tube 4 and the outer tube 6, and thus, the operability of the catheter can be further improved.

Second Embodiment

Figure 6:
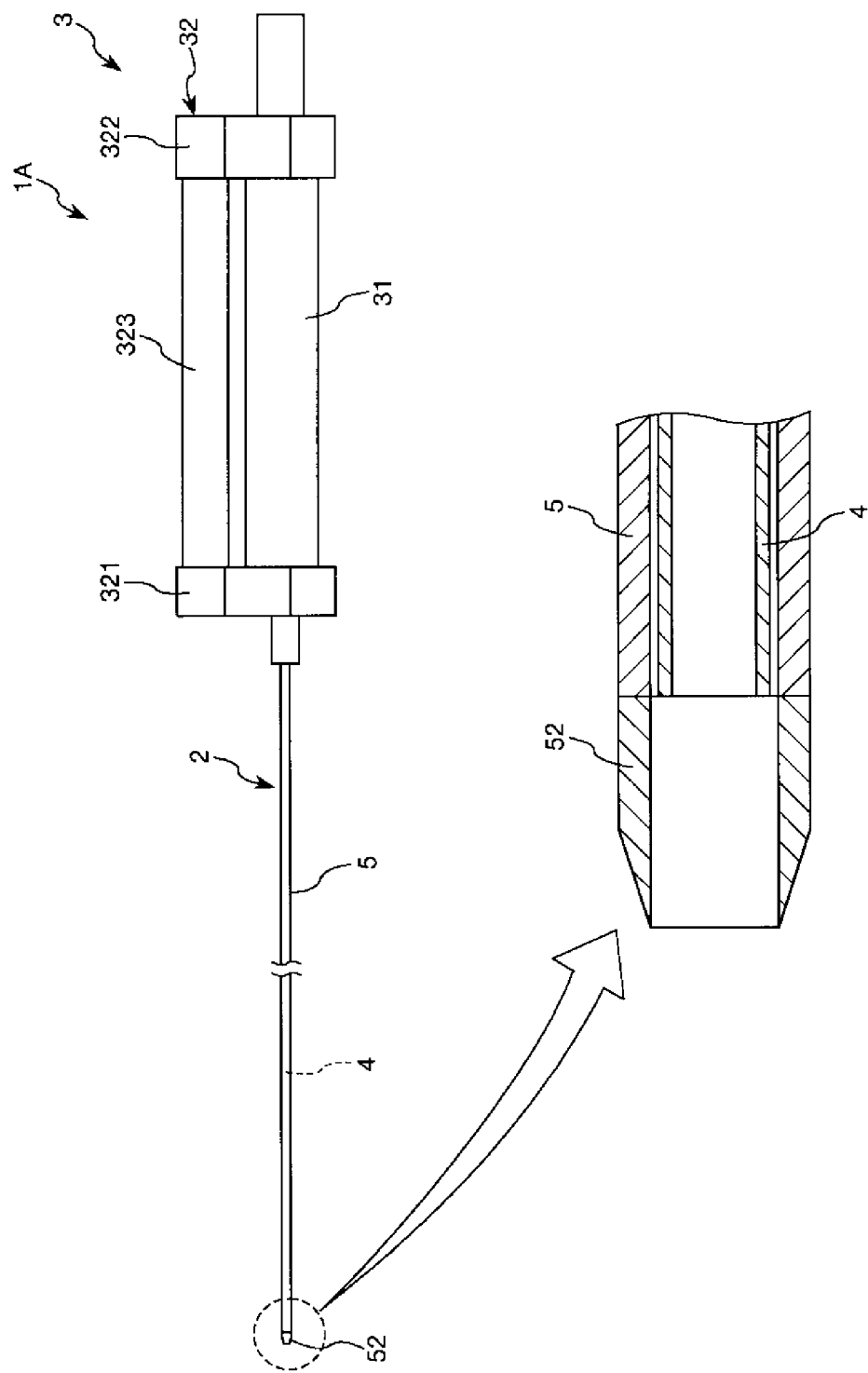
FIG. 6 is a side view illustrating a catheter (second embodiment) according to the present disclosure.

FIG. 6 is a side view illustrating a catheter (second embodiment) according to the present disclosure.

Hereinafter, the second embodiment of the catheter according to the present disclosure will be described with reference to this drawing. However, points different from those in the above-described embodiment will be mainly described, and similar items of the above-described embodiment will be omitted in the description.

The present embodiment is the same as the first embodiment except that the catheter body has a different configuration. This is similarly applicable to the following embodiments.

In a catheter 1A illustrated in FIG. 6, there is no element corresponding to the outer tube 6 according to the first embodiment. Accordingly, the catheter body 2 as a whole can have more improved flexibility. Furthermore, a step difference can be eliminated between the outer tube and the coil tube 5, thereby enabling the catheter body 2 to have a reduced diameter. In addition, the outer peripheral portion of the coil tube 5 is subjected to the hydrophilic treatment described in the first embodiment.

According to the catheter 1A configured in this way, there is no outer tube 6. Accordingly, as illustrated in the enlarged view in FIG. 6, a step difference can be prevented from being formed between the distal tip 52 disposed in the distal end of the coil tube 5 and the coil tube 5. Therefore, the catheter 1A can be prevented from getting caught on the blood vessel or other medical instruments. Furthermore, since there is no outer tube 6, the diameter of the catheter body 2 as a whole can be reduced.

Third Embodiment

Figure 7:
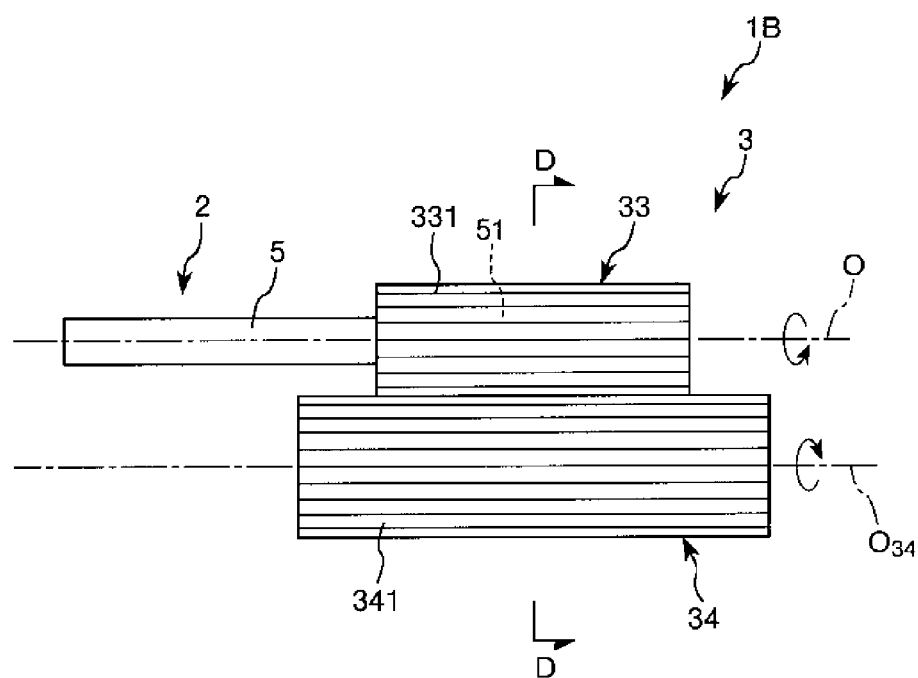
FIG. 7 is a side view illustrating a rotary operation unit included in a catheter (third embodiment) according to the present disclosure.
Figure 8:
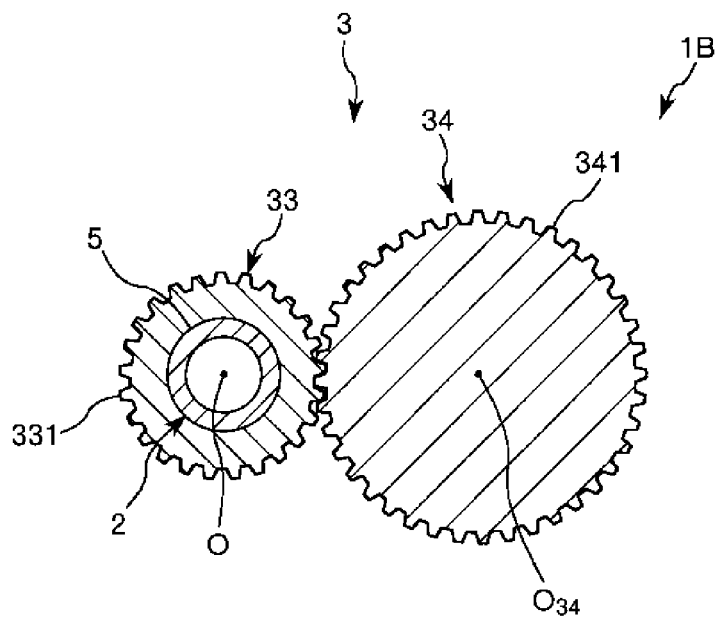
FIG. 8 is a sectional view taken along line D-D in FIG. 7.

As illustrated in FIGS. 7 and 8, in a catheter 1B, the rotary operation unit 3 has a first gear 33 and a second gear 34 meshing with the first gear 33. In FIGS. 7 and 8, a housing or a frame body (support portion) for accommodating the first gear 33 and the second gear 34 is omitted in the illustration.

The first gear 33 is fixed to the proximal portion 51 of the coil tube 5. In addition, the first gear 33 has a columnar shape, and the first gear 33 is located concentrically with the central axis of the coil tube 5. The first gear 33 is rotated, thereby rotating the coil tube 5.

In addition, a tooth 331 extends along the longitudinal direction and is formed along the circumferential direction in the outer peripheral portion of the first gear 33.

The second gear 34 is located on a lateral side of the first gear 33. In addition, the second gear 34 has a columnar shape, and a tooth 341 extends along the longitudinal direction, and the second gear 34 is formed along the circumferential direction in the outer peripheral portion of the second gear 34. The tooth 341 meshes with the tooth 331 of the first gear 33. In this manner, if the second gear 34 performs the rotary operation, the first gear 33 is rotated, and the coil tube 5 can be rotated in response to the rotation of the first gear 33. In this way, the second gear 34 functions as the operation unit for performing the rotary operation.

According to this catheter 1B, in the second gear 34 functioning as the operation unit, a central axis $O_{34}$ of the catheter 1B is shifted from the central axis O of the catheter body 2. In this manner, when the rotary operation is performed, it is possible to prevent the catheter body 2 from hindering the operation.

Fourth Embodiment

Figure 9:
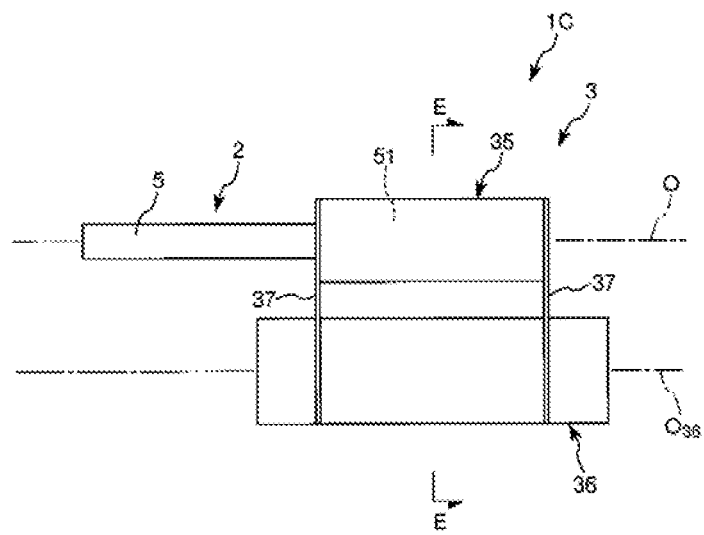
FIG. 9 is a side view illustrating a rotary operation unit included in a catheter (fourth embodiment) according to the present disclosure.
Figure 10:
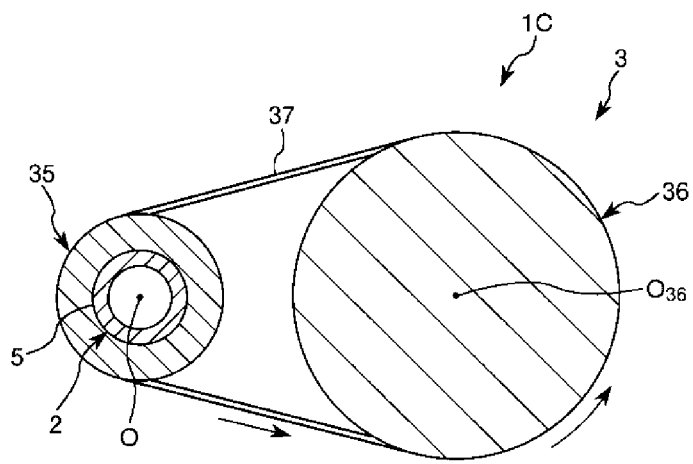
FIG. 10 is a sectional view taken along line E-E in FIG. 9.

As illustrated in FIGS. 9 and 10, in a catheter 1C, the rotary operation unit 3 has a first pulley 35, a second pulley 36, and a belt 37.

The first pulley 35 has a tubular shape, and the proximal portion of the coil tube 5 is fixed to the inside of the first pulley 35. The first pulley 35 is disposed concentrically with the catheter body 2 around the central axis O of the catheter body 2. The second pulley 36 has a columnar shape, and the second pulley 36 is located on the lateral side of the first pulley 35 while being apart from the first pulley 35.

Two belts 37 are wound around the first pulley 35 and the second pulley 36. The belt 37 is wound around the distal portion of the first pulley 35 and the distal portion of the second pulley 36, and the belt 37 is wound around the proximal portion of the first pulley 35 and the proximal portion of the second pulley 36, respectively.

According to the catheter 1C, if the second pulley 36 performs the rotary operation around a central axis $O_{36}$ of the catheter 1C, the rotational force is transmitted to the first pulley 35 via the two belts 37, and the first pulley 35 is rotated. In response to the rotation, the coil tube 5 can be rotated. In this way, the second pulley 36 functions as the operation unit for performing the rotary operation.

According to the catheter 1C configured in this way, the second pulley 36 functioning as the operation unit can be located further away from the central axis O of the catheter body 2. Therefore, when the rotary operation is performed, it is possible to more effectively prevent the catheter body 2 from hindering the operation.

In FIGS. 9 and 10, a housing or a frame body (support portion) for accommodating the first pulley 35, the second pulley 36, and the belt 37 is omitted in the illustration.

Fifth Embodiment

Figure 11:
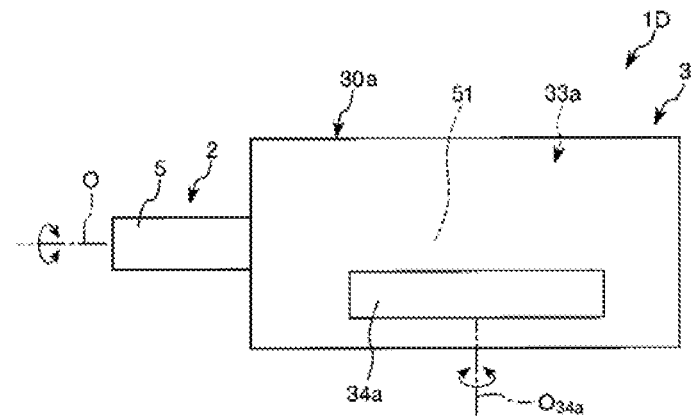
FIG. 11 is a side view illustrating a rotary operation unit included in a catheter (fifth embodiment) according to the present disclosure.
Figure 12:
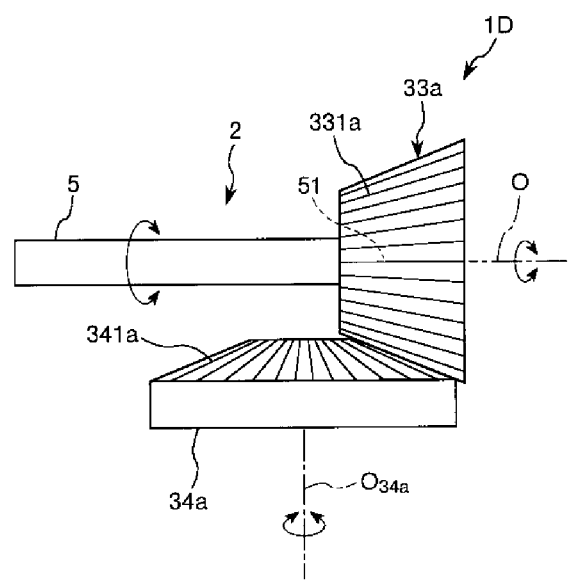
FIG. 12 is a side view illustrating a first gear and a second gear which are illustrated in FIG. 11.

As illustrated in FIGS. 11 and 12, in a catheter 1D, the rotary operation unit 3 has a support portion 30a, a first gear 33a disposed inside the support portion 30a, and a second gear 34a.

The first gear 33a is accommodated inside the support portion 30a. In addition, the first gear 33a is fixed to the proximal portion 51 of the coil tube 5. In addition, the first gear 33a can be a bevel gear having a tooth 331a, and the first gear 33a is located concentrically with the central axis of the coil tube 5. The first gear 33a is rotated, thereby rotating the coil tube 5.

The second gear 34a is located on a lateral side of the first gear 33a. In addition, similar to the first gear 33a, the second gear 34a can be a disc-shaped bevel gear. In addition, the second gear 34a is located in an orientation where a central axis $O_{34}$ of the catheter 1D intersects (i.e., perpendicular to) the central axis O of the catheter body 2.

The second gear 34a has a tooth 341a, and the tooth 341a meshes with the tooth 331a of the first gear 33a. In this manner, if the second gear 34a performs the rotary operation, the first gear 33a is rotated, and the coil tube 5 can be rotated in response to the rotation of the first gear 33a. In this way, the second gear 34a functions as the operation unit for performing the rotary operation. In the second gear 34a, a portion of the outer peripheral portion is exposed from the support portion 30a, and the second gear 34a can perform the rotary operation.

According to the catheter 1D configured in this way, the second gear 34a functioning as the operation unit employs a so-called "dial type", thereby enabling the rotary operation to be minutely and easily adjusted. In addition, a marker indicating a rotation amount can be provided for a portion exposed from the support portion 30a of the second gear 34a, thereby enabling the rotation amount to be easily recognized.

Sixth Embodiment

Figure 13:
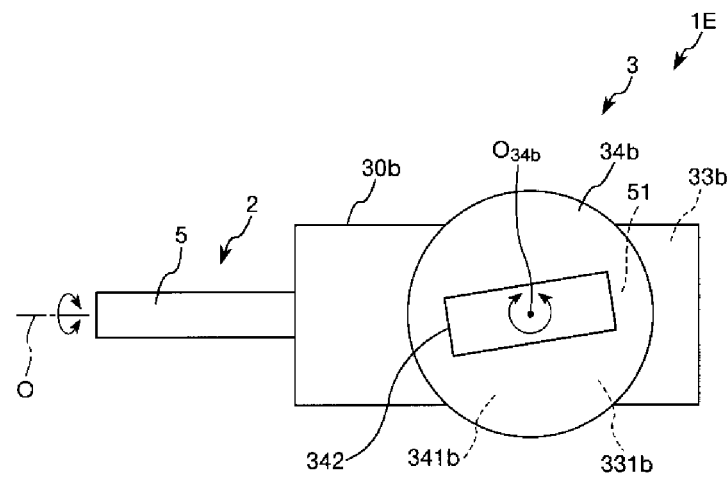
FIG. 13 is a top view illustrating a rotary operation unit included in a catheter (sixth embodiment) according to the present disclosure.
Figure 14:
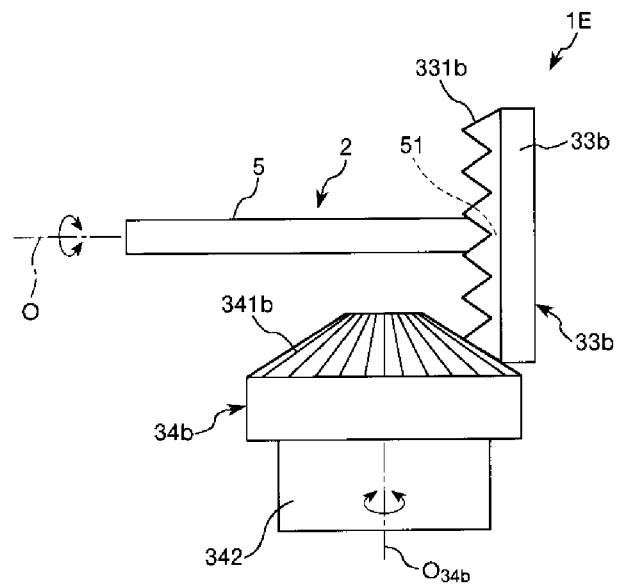
FIG. 14 is a side view illustrating a first gear and a second gear which are illustrated in FIG. 13.

As illustrated in FIGS. 13 and 14, in a catheter 1E, the rotary operation unit 3 has a support portion 30b, a first gear 33b disposed inside the support portion 30b, and a second gear 34b.

The first gear 33b is accommodated inside the support portion 30b. In addition, the first gear 33b is fixed to the proximal portion 51 of the coil tube 5. In addition, the first gear 33b can be a crown gear having a tooth 331b, and is located concentrically with the central axis of the coil tube 5. The first gear 33b is rotated, thereby rotating the coil tube 5.

The second gear 34b is located on a lateral side of the first gear 33b. In addition, the second gear 34b can be a disc-shaped bevel gear. In addition, the second gear 34b is located in an orientation where a central axis $O_{34b}$ of the catheter 1E intersects (i.e., perpendicular to) the central axis O of the catheter body 2.

The second gear 34b has a tooth 341b, and the tooth 341b meshes with the tooth 331b of the first gear 33b. In this manner, if the second gear 34b performs the rotary operation, the first gear 33b is rotated, and the coil tube 5 is rotated in response to the rotation of the first gear 33b. In this way, the second gear 34b functions as the operation unit for performing the rotary operation.

In addition, the second gear 34b has a grip portion 342 formed to protrude in a prismatic shape on a side opposite to the tooth 341b. In this manner, the second gear 34b can be easily operated by gripping the grip portion 342.

In the second gear 34b, a portion (including the grip portion 342) other than the tooth 341b is exposed from the support portion 30b, and the second gear 34b performs the rotary operation. In FIG. 14, the support portion 30b is omitted in the illustration.

According to the catheter 1E configured in this way, similar to the fifth embodiment, the second gear 34b functioning as the operation unit employs a so-called "dial type", thereby enabling the rotary operation to be minutely (i.e., relatively small changes) and easily adjusted.

Hitherto, the catheter according to the present disclosure has been described above with reference to the illustrated embodiments. However, the present disclosure is not limited thereto. Each configuration element of the catheter can be substituted with any desired configuration element which can fulfill the same function. In addition, any desired configuration element may be added thereto.

In the above-described respective embodiments, the coil tube has the first coil, the second coil, and the third coil, one by one. However, the present disclosure is not limited to thereto. For example, the coil tube may have two or more coils for each coil.

In addition, in the above-described respective embodiments, the coil tube may be configured so that the wires of the coils having the same inner diameter and outer diameter are braided and fixed.

A catheter according to the present disclosure includes an inner tube, and a coil tube disposed on an outer peripheral side of the inner tube and configured to include a coil obtained by winding a wire. The coil tube has at least one first coil, and at least one second coil which is located concentrically with the first coil and whose winding direction of the wire is different from that of the first coil. The inner tube and the coil tube are rotatable relative to each other around a central axis of the catheter. According to the present disclosure, the coil tube is disposed so as to be rotatable relative to the inner tube. Accordingly, the coil tube performs a rotary operation, thereby enabling the overall catheter to perform the rotary operation. That is, the coil tube is responsible for transmitting a rotational force. In addition, the coil tube is configured to include the first coil and the second coil, which have mutually different winding directions. Therefore, if the coil tube is rotated in the direction the same as the winding direction of the first coil, a force is applied to the first coil so that the diameter of the first coil expands and the length of the first coil is shortened. In contrast, a force is applied to the second coil so that the second coil is tightened, decreased in diameter, and increased in length. On the other hand, if the coil tube is rotated in the direction opposite to the winding direction of the first coil, a force is applied to the first coil so that the diameter of the first coil contracts and the length of the first coil is lengthened. In contrast, a force is applied to the second coil so that the diameter of the second coil expands and the length of the second coil is shortened. In this way, according to the present disclosure, even if the coil tube is rotated in any direction, the coil tube has a portion to which the rotational force is likely to be transmitted. Therefore, the rotational force can be efficiently transmitted to a distal end of the coil tube.

The detailed description above describes a catheter inserted into a biological lumen, and particularly relates to a catheter for guiding a medical device such as a treatment catheter to a target site in a lumen of a body/living body. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter, the catheter comprising:
an inner tube;
a coil tube disposed on an outer peripheral side of the inner tube, the coil tube being a wound wire coil, the coil tube having at least one first coil and at least one second coil, the at least one second coil being located concentrically with the at least first coil and whose winding direction of the wound wire coil is different from that of the at least one first coil;
the inner tube and the coil tube being rotatable relative to each other around a central axis of the coil tube; and an outer tube disposed on an outer peripheral side of the coil tube, the outer tube and the coil tube being rotatable relative to each other around the central axis of the coil tube.

2. The catheter according to claim 1, further comprising:
a gap between the inner tube and the coil tube when no external force is applied to the catheter.

3. The catheter according to claim 1, wherein the at least one second coil is located inside the at least one first coil.

4. The catheter according to claim 1, further comprising:
a third coil disposed inside the at least one second coil, and wherein the third coil is a wire wound in a direction different from that of the at least one second coil.

5. The catheter according to claim 1, further comprising:
a rotary operation unit fixed to a proximal portion of the coil tube, the rotary operation unit configured to transmit a rotational force to the coil tube.

6. The catheter according to claim 5, wherein the rotary operation unit has a tubular operation tube, and a central axis of the operation tube coincides with the central axis of the coil tube.

7. The catheter according to claim 5, wherein the rotary operation unit has a first gear fixed to the coil tube, and a second gear meshing with the first gear, and the second gear is configured to rotate the coil tube.

8. The catheter according to claim 1, wherein an outer peripheral portion of the outer tube is treated with a hydrophilic coating.

9. The catheter according to claim 1, wherein the inner tube is configured to receive a guide wire, a treatment device, or a liquid material.

10. A catheter, the catheter comprising:
an inner tube having a hollow lumen;
a coil tube disposed on an outer peripheral side of the inner tube, the coil tube having a first coil, a second coil, and a third coil, the second coil being located concentrically with the first coil and whose winding direction is different from that of the first coil, and the third coil being disposed inside the second coil, and wherein the third coil is wound in a direction different from that of the second coil, the inner tube and the coil tube being rotatable relative to each other around a central axis of the coil tube; and
an outer tube disposed on an outer peripheral side of the coil tube, the outer tube and the coil tube being rotatable relative to each other around the central axis of the coil tube.

11. The catheter according to claim 10, further comprising:
a gap between the inner tube and the coil tube when there is no external force applied to the catheter.

12. The catheter according to claim 10, wherein the second coil is located inside the first coil.

13. The catheter according to claim 10, further comprising:
a rotary operation unit fixed to a proximal portion of the coil tube, the rotary operation unit configured to transmit a rotational force to the coil tube.

14. The catheter according to claim 13, wherein the rotary operation unit has a tubular operation tube, and a central axis of the operation tube coincides with the central axis of the coil tube.

15. The catheter according to claim 13, wherein the rotary operation unit has a first gear fixed to the coil tube, and a second gear meshing with the first gear, and the second gear is configured to rotate the coil tube.

16. The catheter according to claim 10, wherein the hollow lumen of the inner tube is configured to receive a guide wire, a treatment device, or a liquid material.

17. A method for guiding a catheter to a target site in a living body, the method comprising:
inserting the catheter into a living body, the catheter including an inner tube and a coil tube disposed on an outer peripheral side of the inner tube, the coil tube being a wound wire coil, the coil tube having at least one first coil and at least one second coil, the at least one second coil being located concentrically with the at least first coil, and a winding direction of the at least one second coil being a different direction from a winding direction of the at least one first coil;
rotating the coil tube relative to the inner tube around a central axis of the coil tube while advancing the catheter in a biological lumen of the living body; and
disposing an outer tube on an outer peripheral side of the coil tube, the outer tube and the coil tube being rotatable relative to each other around the central axis of the coil tube.

18. The method according to claim 17, further comprising:
attaching a rotary operation unit to a proximal portion of the coil tube; and
transmitting a rotational force to the coil tube with the rotary operation unit.

19. The method according to claim 18, wherein the rotary operation unit has a tubular operation tube, and a central axis of the operation tube coincides with the central axis of the coil tube.

20. The method according to claim 18, further comprising:
fixing a first gear of the rotary operation unit to the coil tube;
meshing a second gear with the first gear; and
rotating the coil tube with the second gear.

* * * * *